United States Patent [19]

Niziol

[11] Patent Number: 5,571,214
[45] Date of Patent: Nov. 5, 1996

[54] PROSTHESIS FOR HUMAN FOREARM

[76] Inventor: Edward Niziol, 1731 Harrison La., Youngstown, N.Y. 14174

[21] Appl. No.: 501,235
[22] Filed: Jul. 12, 1995
[51] Int. Cl.$^6$ ........................................ A61F 2/54
[52] U.S. Cl. .................. 623/65; 30/163; 224/232
[58] Field of Search ................ 30/162, 163, 151; 623/65; 224/232

[56] References Cited

U.S. PATENT DOCUMENTS

| 108,596 | 10/1870 | Hundley . | |
|---|---|---|---|
| 110,986 | 1/1871 | Lyman | 30/163 |
| 255,847 | 4/1882 | Fiske | 30/163 |
| 470,777 | 3/1892 | Billings | 30/162 |
| 1,183,413 | 5/1916 | Visel | 623/65 |
| 1,199,052 | 9/1916 | Crawford . | |
| 1,344,357 | 6/1920 | Shirer . | |
| 1,403,281 | 1/1922 | Anover . | |
| 1,701,771 | 2/1929 | Di Stefano | 30/162 |
| 2,284,168 | 5/1942 | Rickenbacher | 30/162 |
| 2,640,260 | 6/1953 | Taylor et al. | 30/162 |
| 2,735,176 | 2/1956 | Costin | 30/162 |
| 3,490,078 | 1/1970 | Perez, Jr. | 623/65 |
| 4,005,525 | 2/1977 | Gringer . | |
| 5,023,996 | 6/1991 | Pape et al. . | |
| 5,344,424 | 9/1994 | Roberts et al. | 30/162 |

FOREIGN PATENT DOCUMENTS

| 342830 | 10/1921 | Germany | 623/65 |
|---|---|---|---|
| 100582 | 8/1923 | Switzerland | 623/65 |

Primary Examiner—Michael J. Milano
Attorney, Agent, or Firm—James F. Mudd

[57] ABSTRACT

A human forearm prosthesis is disclosed which has attached thereto a device comprising a housing, a knife blade suitable for cutting food, a projection on the knife blade for restraining the travel of the knife blade into the housing when it is desired to retract the knife blade into the housing for storage thereof, and out of the housing when it is desired to extend the knife blade for use of the knife blade for cutting food. Preferably, the knife blade moves into and out of the housing by force of gravity. The travel of the knife blade is restrained by a guide slot which extends substantially the length of the housing and a projection located on or near the back end of the knife blade, which projection travels in the guide slot. The device of the invention has a spring operated knife blade release mechanism that blocks the knife blade from passing out of the housing when it is desired to restrain the blade in retracted position. The spring operated blade release mechanism permits the knife blade to protrude or extend from the housing. The mechanism projects through an aperture or hole in the knife blade near the rear end of the knife blade. The spring operated blade release mechanism comprises a spring operated plunger which is attached to the housing which permits a projection in the plunger to extend into the housing to block the travel of the knife blade in the housing.

2 Claims, 4 Drawing Sheets

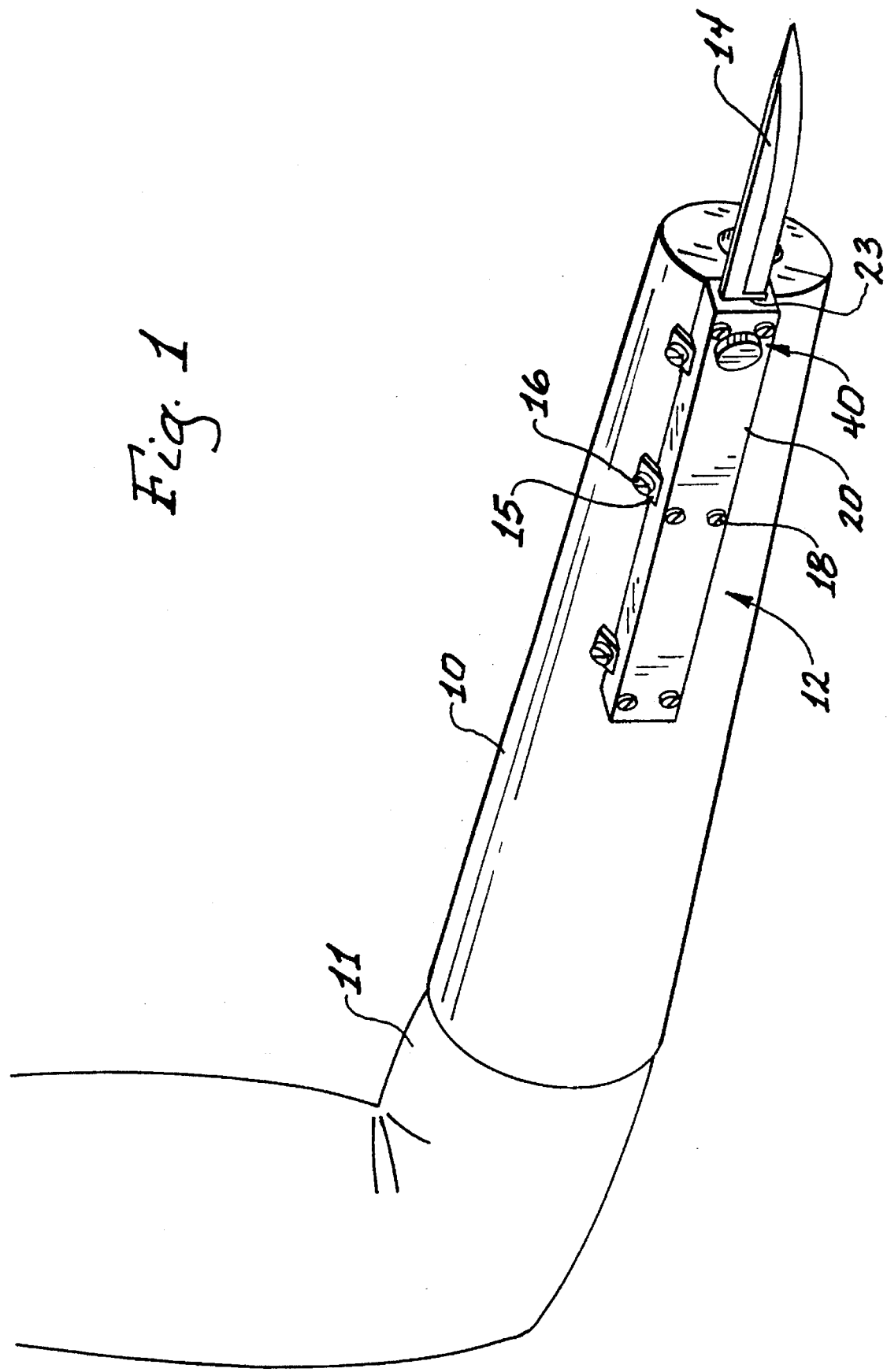

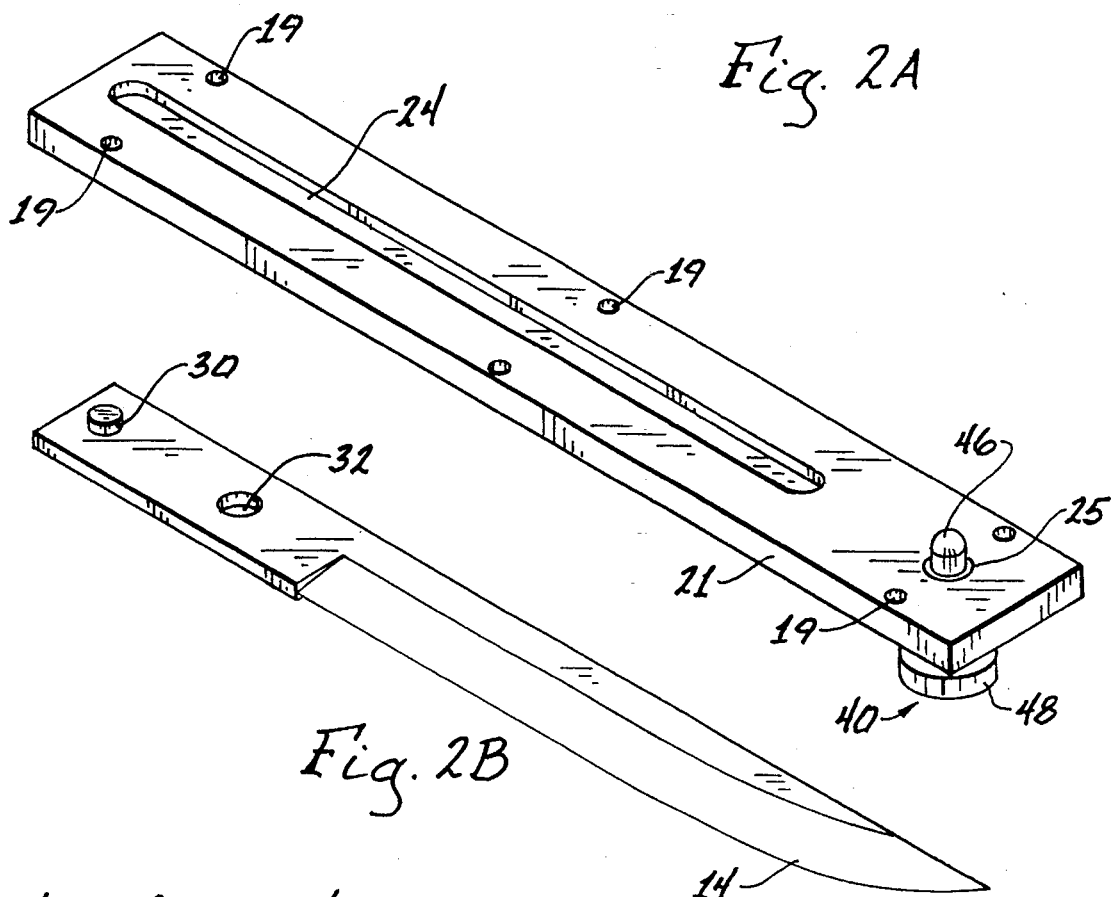
Fig. 2A
Fig. 2B
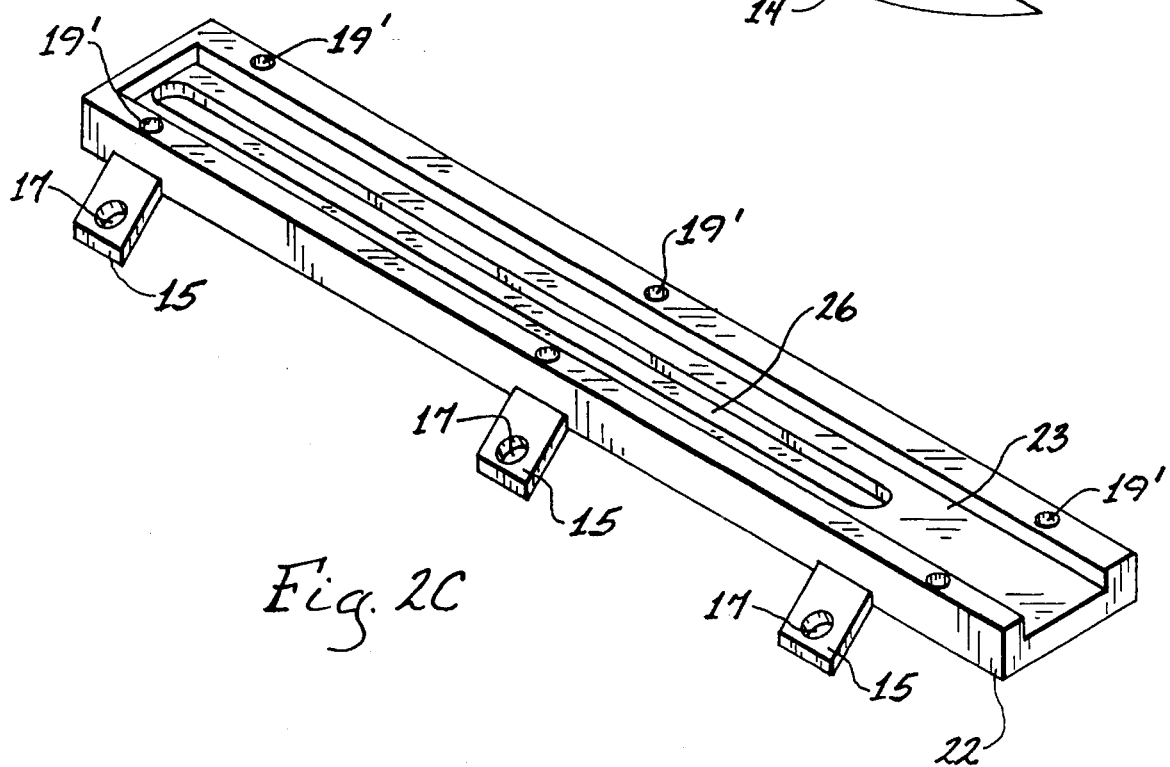
Fig. 2C

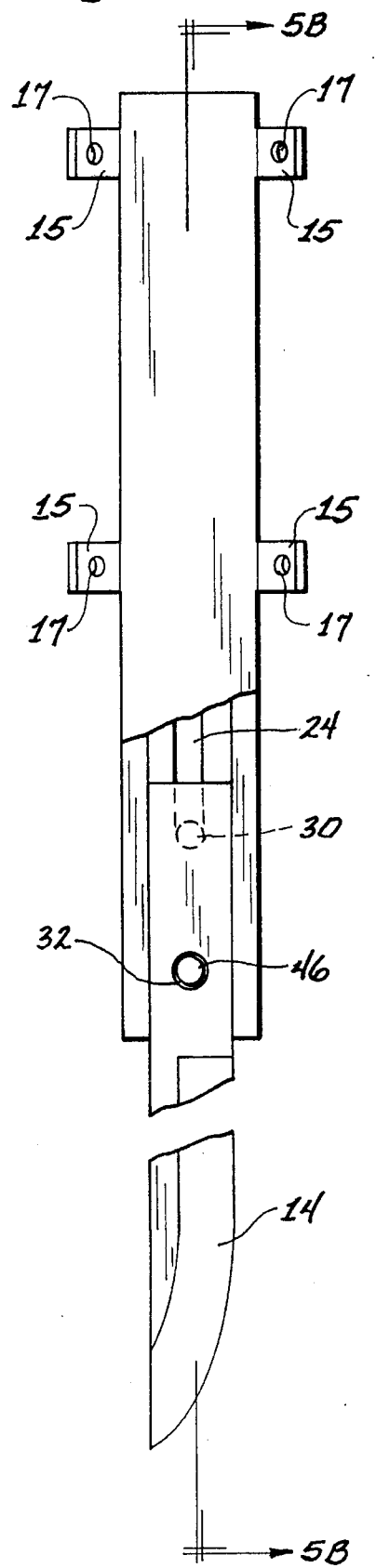
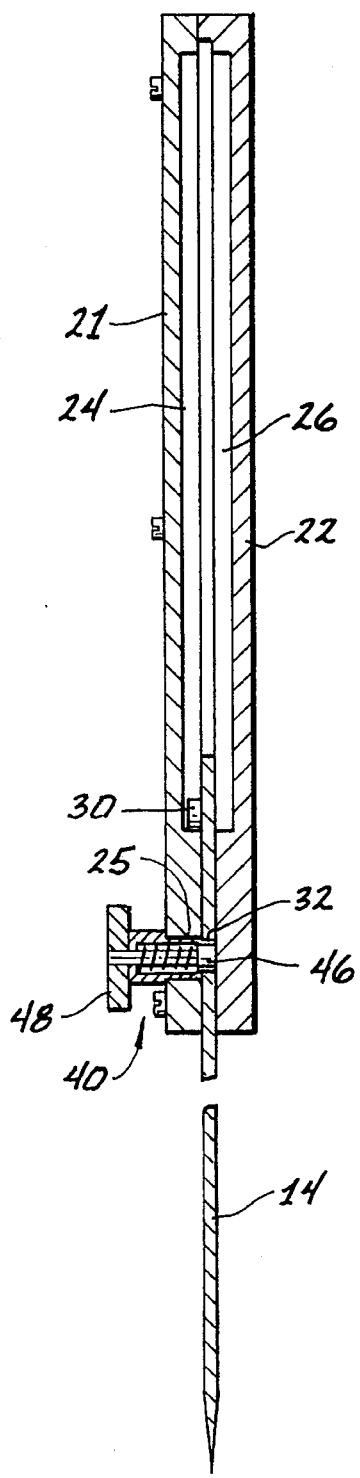

PROSTHESIS FOR HUMAN FOREARM

BACKGROUND OF THE INVENTION

1. The Field of the Invention

This invention relates to a prosthesis for a human forearm that is equipped with a device for cutting food into convenient sized pieces for eating.

2. The Prior Art

The prior art teaches forearm prostheses which have attachments for cutting food into pieces.

U.S. Pat. No. 1,199,052 to Crawford discloses a clamping device attached to a forearm prosthesis for temporary attachment of articles to a prosthesis. Since articles are only temporarily attached to the device of Crawford, it is necessary for the user to carry the various components separately and to store them separately when not in use. Furthermore, the Crawford components project awkwardly from the apparatus and have a set screw 8 which would tend to catch onto other objects when attached permanently. It is necessary to carry the components separately, and it is very inconvenient if one of the components is forgotten by the user.

U.S. Pat. No. 1,344,357 to Shirer discloses another temporary clamping device that is wrapped around a forearm prosthesis and has various clamps for attachment of articles such as a knife, fork, spoon or other instrument. The clamping device is attached only when needed for use. The device requires separate assembly for use. It is necessary for the user to carry the items separately, which makes it very inconvenient if any of the components are forgotten by the user.

U.S. Pat. No. 108,596 to Hundley discloses a "pocket knife" as stated in the title, but does not suggest use of a forearm prosthesis. The "pocket knife" has multiple knife blades in a casing that can be opened about a hinged construction for one blade at a time. This multiplicity of blades leads tho a complex structure. Hundley's structure would be difficult to use unassisted, by double amputees.

U.S. Pat. No. 1,403,281 to Artover is also directed to a pocket knife with a blade that can be withdrawn or retracted into a casing. The blade does not appear to move by the force of gravity, and has a locking member adapted for engagement with a suitable receiver at opposite ends of the handle. Andover appears to require a thumb grasp for moving a knife blade out of the recess in the handle. The knife blade does not appear to travel by gravity. The patent does not suggest use with a prosthesis.

U.S. Pat. No. 4,005,525 to Gringer is directed to a heavy duty hand held utility knife used for cutting carpet, linoleum, and the like. Cringer discloses an elaborate device that uses replacement blades of the type used in common utility knives expanded by a sliding action, and returned to the case, Cringer has short blades that would not be suitable for cutting food into smaller, edible pieces. There is no suggestion of use of the Gringer device with a prosthesis. A cutting tool that is similar to the tool disclosed by Gringer has been marketed by the Stanley Tools division of The Stanley Works, New Britain, Conn.

U.S. Pat. No. 5,023,996 to Pape is directed to a multiple blade handsaw. Pape shows a combination saw and knife with retractable blades and saw types that fold unto a single unit. The Pepe device is a hand held saw and is not suitable for use of the device with a prosthetic device. A pair of blade housings is provided for different types of contingencies. Use with prosthetic devices is not suggested.

The object of this invention is to provide an improved prosthetic device which is useful for cutting food into convenient sized particles that are appropriate for eating.

Another object of the invention is to provide an improved human forearm prosthesis that has a cutting mechanism that is a permanent part of the prosthesis and does not require separate assembly whenever the prosthesis is used.

A further object of the invention is to provide a prosthesis with a cutting device wherein the cutting knife travels by gravity within the cutting blade housing mechanism.

Another object of the invention is to provide a cutting mechanism that is locked into place so that a cutting blade does not inadvertently slide out of its housing when the apparatus of the invention is used to cut food.

A still further object of the invention is to provide a cutting mechanism that is locked in to place when the apparatus of the invention is not being used to cut food.

SUMMARY OF THE INVENTION

These and other objects are accomplished by a human forearm prosthesis, having attached thereto a device comprising a housing, a knife blade suitable for cutting food, means for restraining the travel of the knife blade into said housing when it is desired to retract said knife blade into said housing for storage thereof, and out of said housing when it is desired to extend the knife blade for use of the knife blade for cutting food. Preferably, the knife blade moves into and out of the housing by force of gravity.

The device of the invention has a first means for restraining the travel of the knife blade which comprises guide means which run substantially the length of said housing and a projection located at or near the back end of the knife blade, which projection travels in said guide means when the knife blade moves.

The device of the invention has a second means for restraining the travel of said knife blade which comprises a spring operated knife blade release mechanism that blocks the knife blade from passing out of the housing when it is desired to restrain the blade in the retracted position. The spring operated blade release mechanism permits the knife blade to protrude or extend from the housing when it is desired to use the knife blade for cutting food. The release mechanism has a means which projects through an aperture or hole in the knife blade near the back end of the knife blade to lock the knife blade in place.

BRIEF DESCRIPTION OF THE DRAWINGS

FIG. 1 shows a preferred embodiment of the invention in a perspective view, in which the apparatus of the invention is positioned for use in cutting food.

FIG. 2A shows the top plate of the cutting device of the invention in the inverted form to better display the underside of the top plate.

FIG. 2B shows the knife blade of the cutting device of the invention.

FIG. 2C shows the bottom housing of the cutting device of the invention.

FIG. 5A is a partial cutaway view of the cutting device of the invention shown with the knife blade in the extended position.

FIG. 5B is a sectional view taken along line 5B of FIG. 5A, of the cutting device of the invention shown with the knife blade in the extended position.

DETAILED DESCRIPTION OF THE DRAWINGS

Figure 3A:
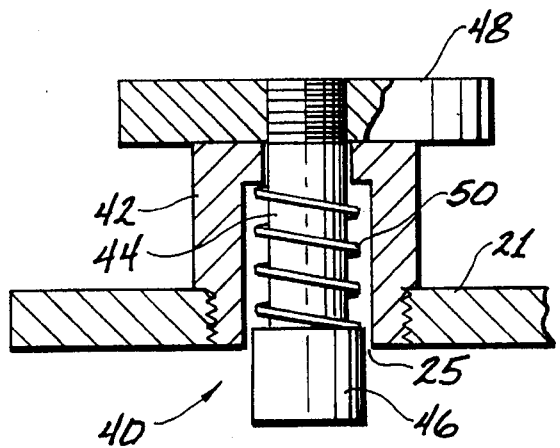
FIG. 3A is a partial sectional view of the knife blade release mechanism of the cutting device of the invention.

FIG. 1 shows a preferred embodiment of the invention where there is attached to a human forearm 11 a prosthesis 10 that is fitted with a cutting device 12 which enables an amputee to cut food into pieces.

The cutting device 12 comprises an elongated housing 20 which is attached to prosthesis 10 with the aid of tabs 15 and screws 16. In FIG. 1, a knife blade 14 is shown in the extended position suitable to cut food into pieces suitable for eating. Blade release mechanism 40 is capable of locking up the knife blade 14 in the extended or retracted position, as desired.

FIG. 2A, FIG. 2B and FIG. 2C show basic elements of the cutting device of the invention. Top plate 21 and bottom housing 22 form cavity 23 when assembled by means of screws 18 (shown in FIG. 1 ) which pass through screw holes 19 and 19' in top plate 21 and bottom housing 22, respectively. Within cavity 23 is situated knife blade 14 which is free to move by gravity into and out of cavity 23.

Figure 4A:
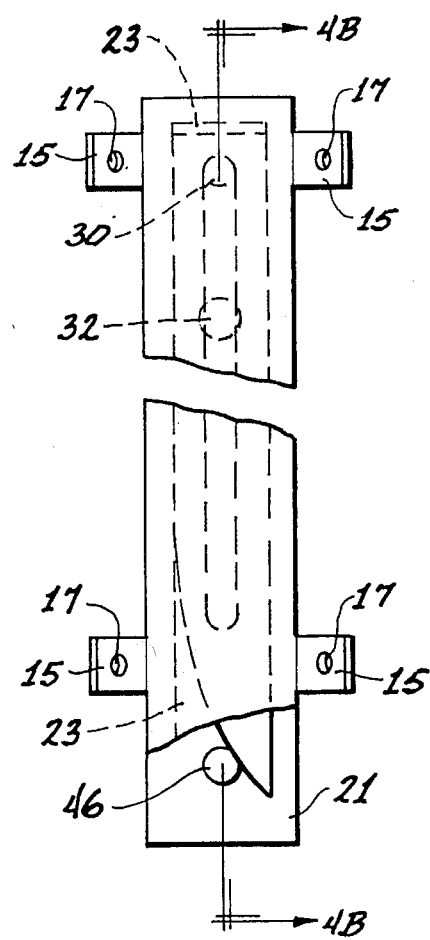
FIG. 4A is a partial cutaway view looking up at the bottom of the cutting device of the invention, showing the knife blade in the retracted position.

To the back end of knife blade 14 is attached a protrusion or button 30 which travels in a guide slot 24 or 26 which arrangements prevent the knife blade 14 from sliding out of the guide slots 24 or 26 and then completely out of the cavity 23. The bottom housing 22 is attached to the prosthesis by means of screws 16 (shown in FIG. 1) which pass through holes 17 in tabs 15 which are firmly attached to the prosthesis 11, but can be removed for cleaning purposes. The tabs 15 with holes 17 are also shown in FIG. 4A and FIG. 5A. The tabs 15 are formed during the machining operation which forms the bottom housing 22.

Figure 3B:
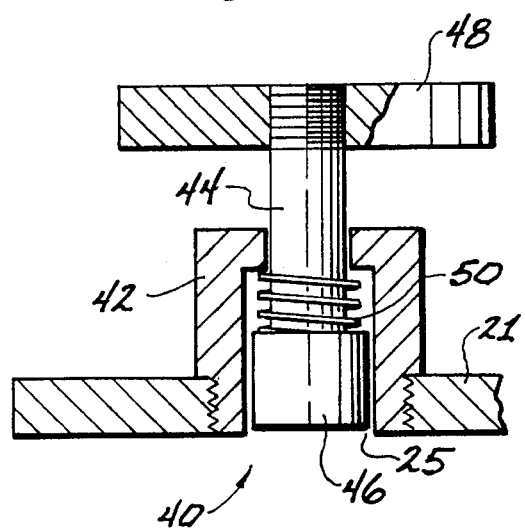
FIG. 3B is a second partial sectional view of a knife blade release mechanism of the cutting device of the invention.

Further control of the travel of the knife blade 14 is exerted by blade release mechanism 40, shown in detail in FIG. 3A and FIG. 3B. Blade release mechanism 40 comprises a release piston 44 positioned within a housing 42 that is attached in an aperture 25 situated in top plate 21. Release piston 44 is firmly attached to release cap 48. Release button 46 is located at the end of piston 44 that is opposite to release cap 48. The piston 44 is raised or lowered against the force of spring 50 which is situated about piston 44.

Figure 4B:
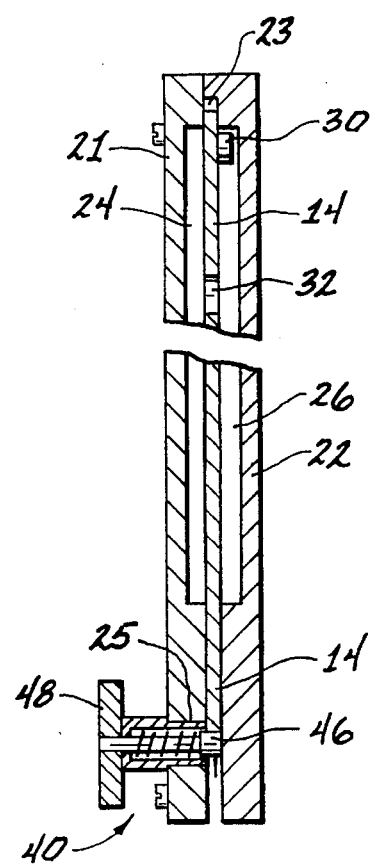
FIG. 4B is a sectional view along a line 4B taken of the cutting device of the invention showing the knife blade in the retracted position.

As shown in FIG. 4A and FIG. 4B, when the knife blade 14 is in the retracted position within cavity 23, the knife blade 14 is held in place by being blocked by release button 46 which protrudes through aperture 25 in the top plate 21 of the housing 20 of the invention.

When it is desired to move the knife blade 14 out of cavity 23, the release cap 48 is pulled in the direction away from the top plate 21 against the force of spring 50 thereby retracting button 46 which has been holding the knife blade 14 in cavity 23. When a person wearing the cutting device 12 pulls the release cap 48 and lowers the cutting device 12 in a substantially vertical position, the knife blade 14 moves most of the way out of the cavity 23, but is retained within the end portion of cavity 23 by the button 46 of the blade release mechanism 40 which locks into hole 32 as shown in FIG. 5A and FIG. 5B. Button 30 which is attached near the back end of the knife blade 14 also serves to hold knife blade 14 in position, as described hereinbefore.

When it is desired to move the knife blade 14 back into cavity 23, the release cap 48 is pulled in a direction away from the top plate 21 against the force of spring 50, thereby retracting button 46 which has been holding knife blade 14 out of the cavity 23. When the person wearing the cutting device 12 raises the cutting device 12 in a substantially vertical position, the knife blade 14 slides back into cavity 23 and is restrained in that position by releasing the button 46 of the blade release mechanism 40. Projection or button 30 which is attached to the back end of the knife blade 14 also serves to hold knife blade 14 in position, as de;scribed hereinbefore.

The blades are reversible depending on whether the prosthesis is on the fight hand or left hand. The knife blade 14 is made reversible by placement or location of projection or button 30 (which is attached to the back end of knife blade 14) in slot 24 or in slot 26.

DETAILED DESCRIPTION OF THE INVENTION

The housing of the invention can be made up of any metal ,preferably a light weight metal, such as aluminum for the comfort of the user, as shown in FIG. 2A and FIG 2C, the housing 20 can comprise a bottom housing 22 and a cover or top plate 21.

The knife blade can be made of conventional metal such as stainless steel or any other suitable metal for quality knives. The guide slots are preferably made of a light metal, such as aluminum. The projection or button 30 should be made of steel, preferably stainless steel, to insure sufficient life of the part. Button 30 can be provided by the head of a screw attached to the knife blade. All other parts are preferably made of steel.

The cutting mechanism of the invention is preferably fixed to the side of the forearm prosthesis. The knife mechanism is intended to be preferably permanently mounted for use when needed. It is a self contained unit, housing and knife in one. The knife blade is gravity fed to slide out of and into the housing. The blade locks in place when extended for use, to prevent it from sliding back into the housing. The device of the invention does not have to be attached for use or detached after use. The user does not have to remember to bring the device of the invention when the user goes out for dinner. Nor does the user need to search for the device of the invention when it is needed. The invention does not require an extra case or purse or pocket for carrying it. The device of the invention is always accessible. The knife blade also locks in place when retracted to prevent it from sliding out of the housing. Having the knife blade in the housing and having the housing attached to the prosthesis is intended for convenience of use.

I claim:

1. In combination, a human forearm prosthesis, and attached thereto a cutting device comprising a housing, said housing having a front and back, a knife blade suitable for cutting, first means and second means for restraining the travel of the knife blade into said housing when said knife blade is retracted into said housing to a retracted position, and out of said front of said housing when the knife blade extends from the housing to an extended position for use of the knife blade, wherein said knife blade moves into and out of the housing by force of gravity; wherein said first means for restraining the travel of the knife blade comprises guide means which runs substantially the length of said housing and a projection located on or near the back end of the knife blade, which projection travels in said guide means; wherein said second means for restraining the travel of said knife blade comprises a spring operated knife blade release mechanism that blocks the knife blade from passing out of the housing when it is desired to restrain the blade in a retracted position, but which spring operated blade release mechanism permits the knife blade to protrude from the housing and which mechanism projects through an aperture in the knife blade near the back end of said knife blade, to lock said knife blade in place, when it is desired to use the knife blade, and wherein, said spring operated knife blade release mechanism is attached to an aperture in said housing located in said front of the housing and said knife blade release mechanism remains in the: aperture in the front of the housing when the knife blade moves from the retracted position to the extended position.

2. A cutting device comprising a housing, said housing having a front and back, a knife blade suitable for cutting, first means and second means for restraining the travel of the knife blade into said housing when said knife blade is retracted into said housing to a retracted position, and out of said front of said housing when the knife blade extends from the housing to an extended position for use of the knife blade, wherein said knife blade moves into and out of the housing by force of gravity; wherein said first means for restraining the travel of the knife blade comprises guide means which runs substantially the length of said housing and a projection located on or near the back end of the knife blade, which projection travels in said guide means; wherein said second means for restraining the travel of said knife blade comprises a spring operated knife blade release mechanism that blocks the knife blade from passing out of the housing when it is desired to restrain the blade in a retracted position, but which spring operated blade release mechanism permits the knife blade to protrude from the housing and which mechanism projects through an aperture in the knife blade near the back end of said knife blade, to lock said knife blade in place, when it is desired to use the knife blade, and wherein said spring operated knife blade release mechanism is attached to an aperture in said housing located in said front of the housing and said knife blade release mechanism remains in the aperture in the front of the housing when the knife blade moves from the retracted position to the extended position.

* * * * *